United States Patent [19]
Weishaupt et al.

[11] Patent Number: 5,671,317
[45] Date of Patent: Sep. 23, 1997

[54] FIBER OPTIC POSITIONER

[75] Inventors: Kenneth R. Weishaupt, Hamburg; William R. Potter, Grand Island; Leroy Wood, Buffalo, all of N.Y.

[73] Assignee: Health Research, Inc., Buffalo, N.Y.

[21] Appl. No.: 680,936

[22] Filed: Jul. 16, 1996

[51] Int. Cl.⁶ ............................................. G02B 6/46
[52] U.S. Cl. ........................ 385/137; 604/20; 606/15; 606/17
[58] Field of Search .................... 385/136, 137, 385/117, 118; 604/20; 606/15, 16, 17

[56] References Cited

U.S. PATENT DOCUMENTS 3,934,590  1/1976  Campagna et al. .................. 128/233

Primary Examiner—Rodney B. Bovernick
Assistant Examiner—Ellen Eunjoo Kang
Attorney, Agent, or Firm—Michael L. Dunn

[57] ABSTRACT

Method and apparatus for stabilizing a fiber optic relative to the skin surface of a patient so that radiation from the fiber optic strikes a defined surface area on the skin independently of patient movement. The apparatus comprises a polypod support having a fiber optic supporting platform and at least three legs to form a tripod. Each of the legs has two ends, a first of which is secured to the fiber optic supporting platform and the second of which is securely attached to the skin of the patient, either directly or by means of a foot attached to the second end. The method of the present invention comprises attaching a polypod, as above described, to the skin of a patient and irradiating a defined surface area by means of an end of a fiber optic held by the polypod support.

6 Claims, 2 Drawing Sheets

FIBER OPTIC POSITIONER

This invention was made with funding from the National Institute of Health grant number CA55791. The United States Government has certain rights in the invention.

BACKGROUND OF THE INVENTION

This invention relates to fiber optics and more particularly relates to the use of fiber optics for medicinal purposes where the fiber optic is used to deliver radiation to or receive radiation from a patient.

Fiber optics are of increasing importance in both medical imaging and treatment. For example, in the area of photodynamic therapy, where a patient is injected with a photodynamic therapeutic agent followed by irradiation, fiber optics have become a radiation delivery method of choice. As with all new technologies, there have, however, been problems associated with the used of fiber optics as a delivery mechanism.

In particular when a fiber optic, or for that matter other light sources, are used to deliver light energy to the skin of a patient for the purpose of irradiating a particular defined area, e.g. a skin tumor, there has been a problem with movement of the patient resulting in inaccurate delivery which can result in irradiation and irritation or necrosis of nearby healthy tissue.

In the past attempts have been made to immobilize the patient which is not only very uncomfortable due to long times involved in light therapy, but still does not provide the accuracy needed because total elimination of patient movement is impractical if not impossible.

BRIEF DESCTIPTION OF THE INVENTION

Figure 1:
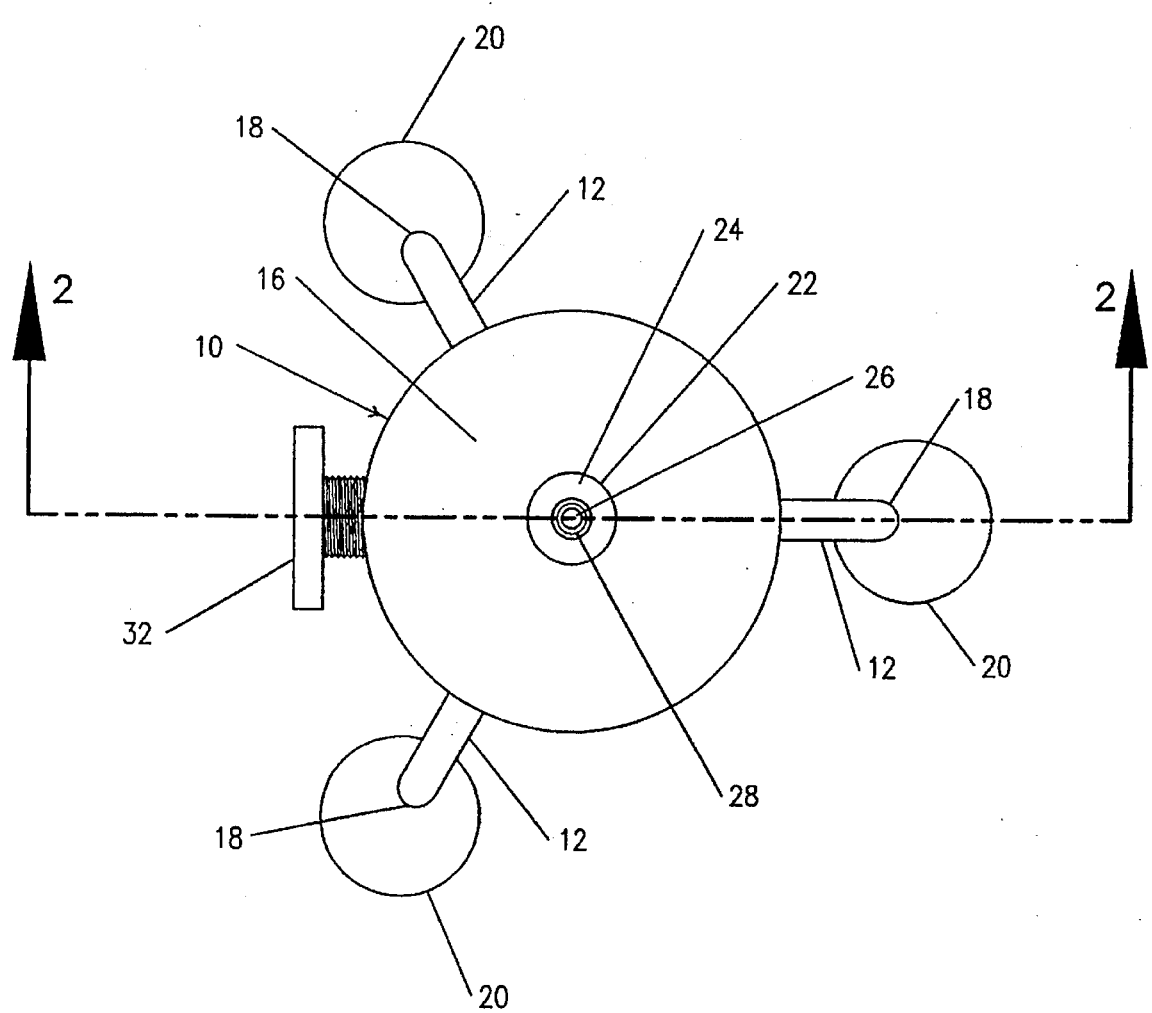
FIG. 1 shows a top view of a tripod in accordance with the present invention.
Figure 2:
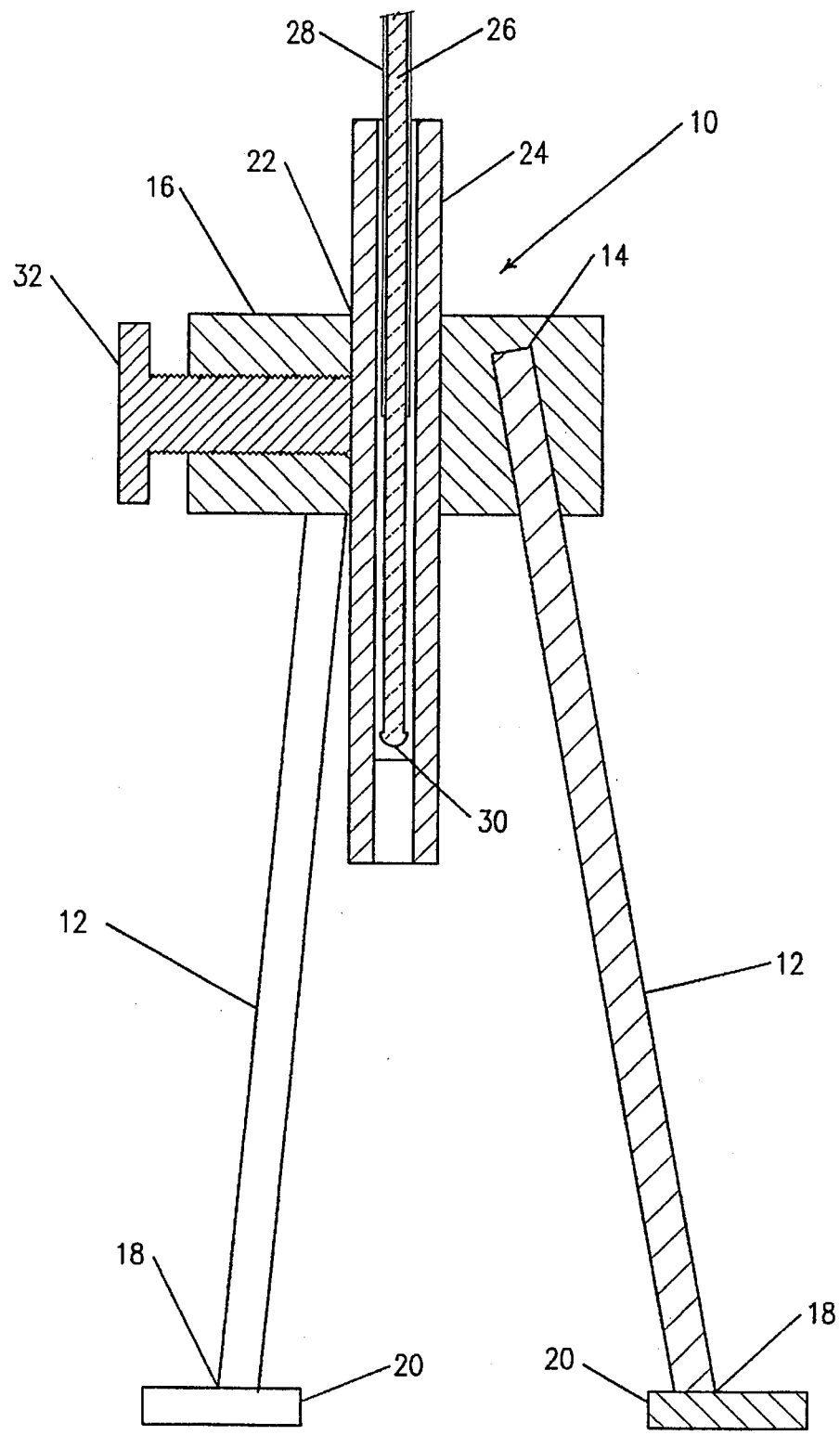
FIG. 2 shows a cross sectional elevational view of a tripod in accordance with the present invention.

In accordance with the invention there is therefore provided a method and apparatus for stabilizing a fiber optic relative to the skin surface of a patient so that radiation from the fiber optic strikes a defined surface area on the skin independently of patient movement. The apparatus comprises a polypod support having a fiber optic supporting platform and at least three legs to form a tripod. Each of the legs has two ends, a first of which is secured to the fiber optic supporting platform and the second of which is securely attached to the skin of the patient, either directly or by means of a foot attached to the second end.

The method of the present invention comprises attaching a polypod, as above described, to the skin of a patient and irradiating a defined surface area by means of an end of a fiber optic held by the polypod support.

DETAILED DESCRIPTION OF THE INVENTION

"Fiber optic" as used herein means not only the fiber optic itself but also includes lenses functioning with the fiber optic, sheathes around the fiber optic and other apparatus necessary or desirable to make the fiber optic function as a light source having a defined impact area upon a skin surface.

"End of the fiber optic" means the area of the fiber optic near the light emitting or receiving portion of the fiber optic which may include supporting material, sheaths and lenses.

"Skin" means any surface area of a patient having a surrounding area large enough to support a polypod of the invention.

"Polypod" means a multileg apparatus. Such a polypod may have from as few as three to an infinite number of legs, e.g. in the form of a supporting cone. The polypod of the invention is usually a tripod or a conical section. In accordance with the invention, the ends of the legs attached to the skin are more distally separated than the ends of the legs attached to the platform and are arranged so that force upon the platform from any direction is resisted by at least one of the legs.

"Vertical", as used herein, means essentially perpendicular to the surface of skin to which a polypod is secured.

"Essentially perpendicular" means an angle of between 60 and 90 degrees to the surface of skin to which a polypod is secured.

In accordance with the invention, the legs may be attached to the skin in any suitable way. The preferred method of attachment is to tape feet upon the surface of the skin or glue them to the skin using a suitable adhesive such as ethylcyanoacrylate, to which the ends of the legs are attached mechanically or by adhesive. Optionally, but not preferably, the legs may be glued directly to the skin or inserted into the skin and supporting muscle.

The invention may be more fully understood by reference to the drawings which illustrate a preferred embodiment of the invention. It is to be understood that the preferred embodiment is for purposes of illustrating and not limiting the present invention.

As seen in the drawings, tripod 10 is provided with legs 12, each of which is attached at a first end 14 to fiber optic platform 16 and at their second ends 18 to feet 20. Platform 16 is provided with a through hole 22 sized to accommodate a tube 24 which contains fiber optic 26 covered by sheath 28. Fiber optic 26, at the end toward the feet 20 also comprises a focusing lens 30. Platform 16 is provided with a means for securing tube 24 in an essentially vertical position (within 10 degrees of vertical) in the form of thumb screw 32.

In operation the feet 20 are glued to the surface of skin surrounding a skin area to be treated. Feet 20 are attached to the skin of a patient usually by means of ethyl cyanoacrylate adhesive. Feet 20 are arranged so that they are essentially equidistant from each other (i.e. arranged at about 120°+/– 10° intervals around platform 16). Furthermore, for stability, the legs extend from the platform toward the skin at an angle of from 10 to 45 degrees from the vertical.

The area of skin to be irradiated is located between feet 20 directly below lens 30. Light passing through fiber optic 26 from a source not shown, through lens 30 to the desired skin area. Movement by the patient is thus rendered essentially irrelevant because the tripod is attached to and moves with the patient thus the relationship between the lens and the desired skin area does not vary.

While the polypod of the invention has been primarily developed for irradiation with light energy in photodynamic therapy, it is to be understood that the invention may also be used for fiber optic or scan imaging or may be used for high energy radiation applications. In such a case electronic scanning apparatus and high energy irradiation sources held by the platform may be considered equivalent to a fiber optic held by the platform, as described herein.

What is claimed is:

1. Apparatus for stabilizing a fiber optic relative to the skin surface of a patient so that radiation from the fiber optic strikes a defined surface area on the skin independently of patient movement, said apparatus comprising a polypod support having a fiber optic supporting platform and at least three legs to form a tripod, each of the legs having two ends, a first end being secured to the fiber optic supporting platform and the second end being adapted for secure attachment to the skin of the patient.

2. The apparatus of claim 1, wherein the polypod is a tripod.

3. The apparatus of claim 2 wherein the second ends of the legs are provided with feet for attachment to the skin.

4. The apparatus of claim 1 wherein the platform is a block having a vertically oriented hole therein sized to accept a fiber optic including a focusing lens.

5. A method for irradiating a desired area of skin of a patient which comprises:

Attaching the second ends of the legs of the apparatus of claim 1 to the skin of a patient arranged so that the second ends are essentially equidistant from each other, the legs extending from the platform toward the skin at an angle of from 10 to 45 degrees from the vertical and so that the area of skin to be irradiated is directly below a fiber optic held by the platform; and Passing light through the fiber optic to the desired skin area.

6. A method for irradiating a desired area of skin of a patient which comprises:

Attaching the feet of the second ends of the legs of the apparatus of claim 3 to the skin of a patient by means of a cyanoacrylate adhesive, said feet being arranged so that the second ends are essentially equidistant from each other, the legs extending from the platform toward the skin at an angle of from 10 to 45 degrees from the vertical and so that the area of skin to be irradiated is directly below a fiber optic held by the platform; and passing light through the fiber optic to the desired skin area.

* * * * *